(12) United States Patent
Morris et al.

(10) Patent No.: US 8,694,300 B2
(45) Date of Patent: Apr. 8, 2014

(54) INDIVIDUALIZED RANKING OF RISK OF HEALTH OUTCOMES

(75) Inventors: Don Morris, Atherton, CA (US); R. Bradley Patterson, Arlington, VA (US); Peter Alperin, San Francisco, CA (US)

(73) Assignee: Archimedes, Inc., San Francisco, CA (US)

( * ) Notice: Subject to any disclaimer, the term of this patent is extended or adjusted under 35 U.S.C. 154(b) by 582 days.

(21) Appl. No.: 12/476,907

(22) Filed: Jun. 2, 2009

(65) Prior Publication Data
US 2010/0198571 A1 Aug. 5, 2010

Related U.S. Application Data

(60) Provisional application No. 61/110,461, filed on Oct. 31, 2008.

(51) Int. Cl.
*G06G 7/58* (2006.01)
*G06F 19/12* (2011.01)

(52) U.S. Cl.
CPC .................................. *G06F 19/12* (2013.01)
USPC ......................................................... 703/11

(58) Field of Classification Search
CPC ......... G06F 19/12; G06F 19/18; G06F 19/20; G06F 19/24; G06F 19/26
USPC .......................................................... 703/11
See application file for complete search history.

(56) References Cited

U.S. PATENT DOCUMENTS

| | | | |
|---|---|---|---|
| 6,108,635 A | 8/2000 | Herren et al. | |
| 6,949,342 B2 * | 9/2005 | Golub et al. | 435/6.14 |
| 7,260,480 B1 | 8/2007 | Brown et al. | |
| 2005/0119534 A1 | 6/2005 | Trost et al. | |
| 2006/0129427 A1 | 6/2006 | Wennberg | |
| 2006/0173663 A1 | 8/2006 | Langheier et al. | |
| 2007/0239490 A1 | 10/2007 | Sullivan | |
| 2008/0015894 A1 | 1/2008 | Miller et al. | |
| 2008/0091471 A1 | 4/2008 | Michon et al. | |
| 2008/0147440 A1 | 6/2008 | Kil | |
| 2008/0275729 A1 | 11/2008 | Taggart et al. | |
| 2009/0150180 A1 | 6/2009 | Cohen et al. | |
| 2009/0254375 A1 | 10/2009 | Martinez et al. | |
| 2009/0326976 A1 | 12/2009 | Morris | |
| 2010/0004945 A1 | 1/2010 | Petratos et al. | |
| 2010/0185399 A1 | 7/2010 | Slotman | |
| 2010/0305964 A1 | 12/2010 | Eddy et al. | |
| 2011/0082350 A1 | 4/2011 | Koh | |
| 2011/0119212 A1 | 5/2011 | DeBruin et al. | |
| 2011/0173027 A1 | 7/2011 | Olszewski et al. | |
| 2011/0199212 A1 | 8/2011 | Matityaho et al. | |

FOREIGN PATENT DOCUMENTS

WO  WO 2005/117553 A2 * 12/2005

OTHER PUBLICATIONS

Singh et al. Gene expression correlates of clinical prostate cancer behavior. Cancer Cell, vol. 1, 2002, pp. 203-209.*
Stephenson et al. Flow cytometry of prostate cancer: Relationship of DNA content to survival. Cancer Research, 1987, vol. 47, pp. 2504-2507.*
Tannock et al. Chemotherapy with mitoxantrone plus prednisone or prednisone alone for symptomatic hormone-resistant prostate cancer: A Canadian randomized trial with palliative end points. Journal of Clinical Oncology, vol. 124, 1996, pp. 1756-1764.*
Notification of Transmittal of the International Search Report and the Written Opinion of the International Searching Authority, or the Declaration received in PCT Application No. PCT/US09/62005 dated Jun. 14, 2010 (11 pages).
Current Claims for PCT Application No. PCT/US09/62005, Jul. 2010 (7 pages).
"DiabetesPHD Personal Health Decisions" downloaded from the Internet on Sep. 1, 2009 < http://www.diabetes.org/diabetesphd/ 1 page.
Bajdik, C. et al., "A computer model to simulate family history of breast/ovarian cancer in BRCA1 mutation carriers" (13 pages), Mathematical Biosciences vol. 171, 2001,pp. 99-111.
Dinh, T. et al., "Health Benefits and Cost Effectiveness of Primary Genetic Screening for Lynch Syndrome in the General Population" (14 pages), Cancer Prev Res, vol. 4, 2010, pp. 1-13.
Sibert, A. et al., "The effect of disease penetrance, family size, and age of onset on family history with application to setting eligibility criteria for genetic testing", Familial Cancer, vol. 2, 2003, pp. 35-42.
"Notification of Transmittal of the International Search Report and the Written Opinion of the International Searching Authority, or the Declaration" received in International application No. PCT/US10/55010 dated Jul. 1, 2011 (8 pages).
Current Claims of International application No. PCT/US10/55010 dated Jul. 2011 (7 pages).
U.S. Appl. No. 12/611,785, filed Nov. 3, 2009, Office Action, Jan. 5, 2012.
U.S. Appl. No. 12/146,727, filed Jun. 26, 2008, Notice of Allowance, Jan. 20, 2012.

(Continued)

*Primary Examiner* — Jerry Lin
(74) *Attorney, Agent, or Firm* — Hickman Palermo Truong Becker Bingham Wong LLP (57) ABSTRACT

An apparatus for creating a graphical representation of personalized healthcare information is provided. A data processing apparatus that has one or more processors is disclosed. Query component logic receives a request comprising patient identification information. Query execution logic, based on the patient information determines a first metric and one or more intervention metrics. The first metric represents a current health related metric for the patient, while the intervention metrics represent a predicted health related metric, assuming that the patient conforms to the intervention. A graphical representation of the two metrics is created.

32 Claims, 5 Drawing Sheets

(56) References Cited

OTHER PUBLICATIONS

U.S. Appl. No. 12/788,242, filed May 26, 2010, Office Action, Feb. 14, 2012.
U.S. Appl. No. 12/788,242, filed May 26, 2010, Notice of Allowance, Jun. 27, 2013.
U.S. Appl. No. 12/611,785, filed Nov. 3, 2009, Interview Summary, Aug. 20, 2012.
U.S. Appl. No. 12/611,785, filed Nov. 3, 2009, Final Office Action, Jun. 19, 2012.
U.S. Appl. No. 12/788,242, filed May 26, 2010, Final Office Action, Oct. 17, 2012.

* cited by examiner

| MRN | Name | Age | Sex | Ben | |
|---|---|---|---|---|---|
| 12X3460 | Polly Patient | 26 | F | 410A 73.55 | ... |
| 32B1654 | Patrick Patient | 59 | M | 410B 25.95 | ... |
| 45A6789 | Petunia Patient | 43 | F | 410C 22.05 | ... |
| 12Y3789 | ... | ... | ... | 22.01 | ... |
| 74P1852 | ... | ... | ... | 21.04 | ... |
| 85C2963 | ... | ... | ... | 18.93 | ... |
| 96S3852 | ... | ... | ... | 17.05 | ... |
| 45T6852 | ... | ... | ... | 12.48 | ... |
| ... | | | | | |

INDIVIDUALIZED RANKING OF RISK OF HEALTH OUTCOMES

CROSS-REFERENCE TO RELATED APPLICATIONS; BENEFIT CLAIM

This application claims the benefit under 35 U.S.C. §19(e) of Provisional Appln. 61/110,461, filed Oct. 31, 2008, the entire contents of which is hereby incorporated by reference as if fully set forth herein.

TECHNICAL FIELD

The present disclosure generally relates to computers configured to perform healthcare process analysis. The disclosure relates more specifically to techniques useful in such computers for associating intervention data with simulated healthcare processes.

BACKGROUND

Currently the great majority of decisions in healthcare are made with an imperfect understanding of their consequences. At the individual level, physicians' perceptions of their patients' risks and the effects of treatments vary widely, with corresponding effects on practice patterns. At the population level, guidelines, performance measures, incentives, and disease management programs are launched with little if any knowledge of their potential effects.

The Archimedes Model, commercially available through professional services from Archimedes, Inc., San Francisco, Calif., is a well-validated, realistic simulation of human physiology and disease and healthcare systems. These characteristics enable the Model to support research and decision-making about healthcare systems and policy at a level of detail previously not possible.

The Archimedes Optimizer, commercially available from Archimedes, Inc., is a computer-based decision support tool designed to give doctors, care managers and patients an accurate individualized assessment of the health benefits of preventive pharmaceutical and behavioral interventions such as blood pressure medications or weight loss. The Archimedes Optimizer is based on the Archimedes Model and uses as input, patient or health plan member data including demographic information, biomarkers, medication history, and behaviors which are extracted from the electronic medical record or other similar databases. The Archimedes Optimizer's output is designed to be shared with the member as well as the healthcare provider.

Quantitative information about the current adverse health outcome risk and the risk reduction of specific interventions has not been available to either physicians or their patients before the Archimedes Optimizer. As a result of this lack of information, interventions are often not prescribed to patients who would benefit greatly from the intervention and prescribed to others who would benefit very little.

Even when the intervention is correctly prescribed, the lack of quantitative information makes it difficult for a medical practitioner to effectively convey intervention information to a patient, and efforts to do so may be misinterpreted by the patient. The result is sub-optimal health for a patient who, due to this misinterpretation, fails to act on a suggested intervention or misapplies the information provided.

Furthermore, the current methods used to convey the results of medical interventions, such as taking a particular drug or losing weight, are dependent on the knowledge of the doctor of the effects of the interventions and the interaction and overlap of the interventions for a person with characteristics that are similar to those of the patient. This reliance on the practitioner to be able to convey such details to the patient coupled with the possibility of misinterpretation by the patient exposes multiple degrees of human error capable of reducing the quality of life of the patient.

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

DETAILED DESCRIPTION

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

The entire disclosures of U.S. patent application Ser. No. 12/146,727, "Estimating Healthcare Outcomes For Individuals," U.S. Pat. No. 7,136,787, U.S. Patent Publication No. 20070038475, "Dynamic healthcare modeling," U.S. Patent Publication No. 20050288910, "Generation of continuous mathematical model for common features of a subject group," and U.S. Patent Publication No. 20050125158, "Generating a mathematical model for diabetes," form a part of the present disclosure and are hereby incorporated by reference in their entirety for all purposes as if fully set forth herein.

Interventions

A medical intervention represents a change (such as starting a drug, surgery, weight loss, or exercise) that is associated with the health of a patient. The Archimedes Optimizer is capable of supporting any number of interventions. Some examples of interventions relating to treatment of cardiovascular disease and/or diabetes are the following classes of pharmaceuticals: ACE inhibitor; Aspirin; Beta blocker; Calcium channel blocker; Diuretic; ACE inhibitor/diuretic combination; Statin; Insulin; Oral diabetes medication; and the following behavioral changes: Weight loss; Smoking cessation.

Interventions are not required to have a positive effect. For example, an intervention may represent weight gain, increase in smoking, or a sub-optimal dose of medications, or may have both positive and negative effects such as an anti-psychotic medication that increases cardiovascular risk.

Health Related Metrics

Health related metrics are quantitative assessments of health that may combine several medical characteristics that hold meaning for a patient. Health related metrics include years of life remaining (life-years), quality of life, quality-of-life adjusted life-years, and event metrics that measure the likelihood of individual events such as myocardial infarction, stroke, diabetes, renal failure, amputation, and blindness. Events measured by event metrics may be adverse or favorable. An example of a favorable event is achieving pregnancy. Other health related metrics are weighted combinations of the above designed to reflect the total health impact of a change in a balanced way. The Archimedes Optimizer uses benefit scores are weighted sums of the likelihoods of different outcomes within a certain time period. The weights associated with each of the outcomes are based on a health related quality of life (HRQoL) measure such as the EQ-5D score, and other publications, and supplemented by the risk of death associated with each outcome.

The benefit score of an intervention measures the difference in the predicted quality of life score in five years if the patient receives the intervention compared to the predicted quality of life score in five years if they do not. Quality of life scores ordinarily range between zero and one. A healthy person has a quality of life score of one, and a quality of life score of zero represents death. The Archimedes Optimizer multiplies these scores by one thousand to put them on a larger scale (0 to 1000). In one embodiment, the Optimizer calculates scores for multiple time windows (e.g. five, ten, and thirty years). The healthcare provider or patient may be able to select the window of choice or use a default selection based on the age of the patient.

The benefit score of an intervention is a weighted combination of the decrease in risk of outcomes due to the intervention. Weights are selected to approximate the expected difference in the quality of life five years in the future if the patient received the intervention vs. at the end of the five-year period if the patient did not receive the intervention. For example, in a diabetic who is hypertensive, ACE inhibitors are beneficial in reducing the risk of heart attacks and strokes, as well as end stage renal disease. To calculate the benefit of ACE inhibitors, the reduction in risk of each of these outcomes is combined using the quality weights assigned to the outcomes and the likelihood of death associated with each of the outcomes.

The total benefit score is calculated as a weighted combination of the decrease in risk of outcomes due to the patient taking all interventions that have reported benefit. It is the expected difference in the quality of life at the end of a five-year period during which the patient received all beneficial interventions vs. at the end of a five year period during which the patient did not receive any of them.

In an embodiment, the total benefit score is not the sum of the individual intervention benefits. The Archimedes Optimizer computes new risk predictions for the combination of interventions. It uses these new predicted risks to estimate the difference in health related metrics such as the quality of life score if a patient were to adhere to all of the interventions.

In an embodiment, the Archimedes Optimizer is based at least in part on a very large representative virtual population that is simulated in the Archimedes Model for a virtual time period of five years. In an embodiment, the Model is configured to simulate a population of millions of individuals. The risks reported for a real patient are based on that patient's demographics, vital signs, lab results, and drug history and are derived from the outcomes seen in the simulation of individuals in the virtual population that have demographics, vital signs, lab results, and drug history that are similar to the real patient.

In another embodiment, the Archimedes Optimizer is not based on a simulated virtual population. For example, the Archimedes Optimizer may be based on a database of patient information that reflects actual demographics, vital signs lab results, and drug history of actual patients in a particular region, hospital, or other grouping. As another example, the Archimedes Optimizer may be based on a projected actual population that combines trends and statistics related to a geographical region with actual patient data.

Risks and benefits are calculated for a 5-year period, and based on the assumption that the member begins the intervention today and continues to receive it with 100% compliance for the next five years. Smoking cessation assumes that there is no recidivism. The weight loss intervention is based on an expectation that the member will regain most of the lost weight over a period of a few years. The actual weight loss over time and the impacts of this weight loss on various biomarkers have been modeled based on the changes seen in the Diabetes Prevention Program and another a four-year study of the effects of weight loss.

The risk of an outcome in a normal healthy individual of the same age and gender as the patient is provided for comparison in the member reports. This is calculated as the $n^{th}$ percentile (currently n=10) of the risk distribution in the patient subpopulation of that age and gender.

Structural and Functional Overview

Figure 1:
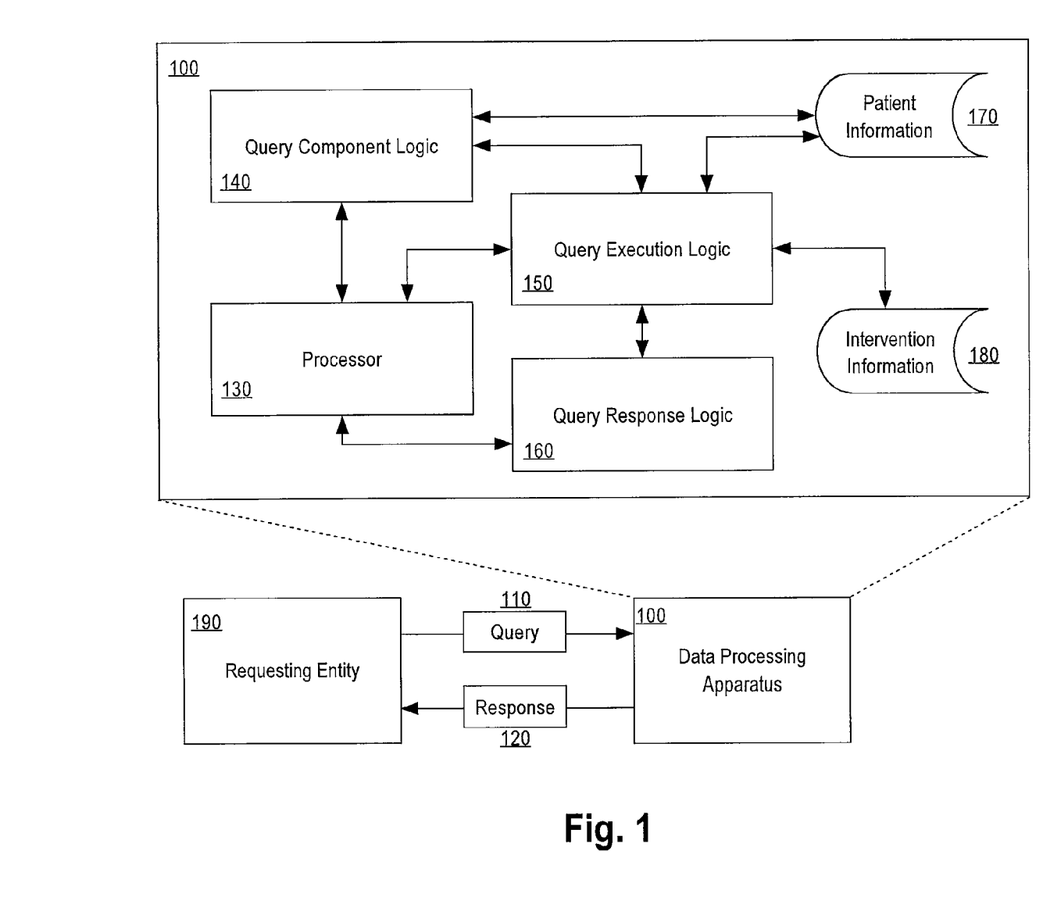
FIG. 1 illustrates an apparatus on which an embodiment may be implemented.

FIG. 1 represents a data processing apparatus 100 on which an embodiment may be implemented. A query 110 is sent to the data processing apparatus 100 by requesting entity 190. The requesting entity 190 may reside on or be coupled to the computer on which the data processing apparatus 100 resides or may reside on a separate computer such as a healthcare practitioner workstation or the personal computer or portable computing device of a patient. In an embodiment, the requesting entity 190 is a web browser. In response to the query 110, a response 120 is sent to the requesting entity 190.

The data processing apparatus comprises a processor 130, which is coupled to query component logic 140, query execution logic 150, and query response logic 160. A repository of patient information 170 is coupled to or accessible to the query component logic 140 and query execution logic 150. A repository of intervention information 180 is coupled to or accessible to the query execution logic.

The query component logic 140 is coupled to the processor 130, and in operation, receives a query 110 comprising patient identification information 170 associated with a patient. Query execution logic 150, based on the patient information 170 determines a first metric based at least in part on the patient identification information. The first metric represents a current health related metric value for the patient. For example, the first metric may represent an event metric that measures the current likelihood that the patient will experience a heart attack within the next five years. The query execution logic 150 also determines one or more intervention metrics, each based at least in part on an associated medical intervention and the patient identification information, and derived from intervention information 180, and representing a predicted health related metric, assuming that the patient conforms to the intervention. A graphical representation concurrently displaying the various metrics is created. In an embodiment, query response logic 160 electronically sends a response that causes a computer to create a graphical representation based on the first metric and the one or more intervention metrics, wherein the graphical representation concurrently presents the first metric and the one or more intervention metrics.

Graphical Representation

Figure 2:
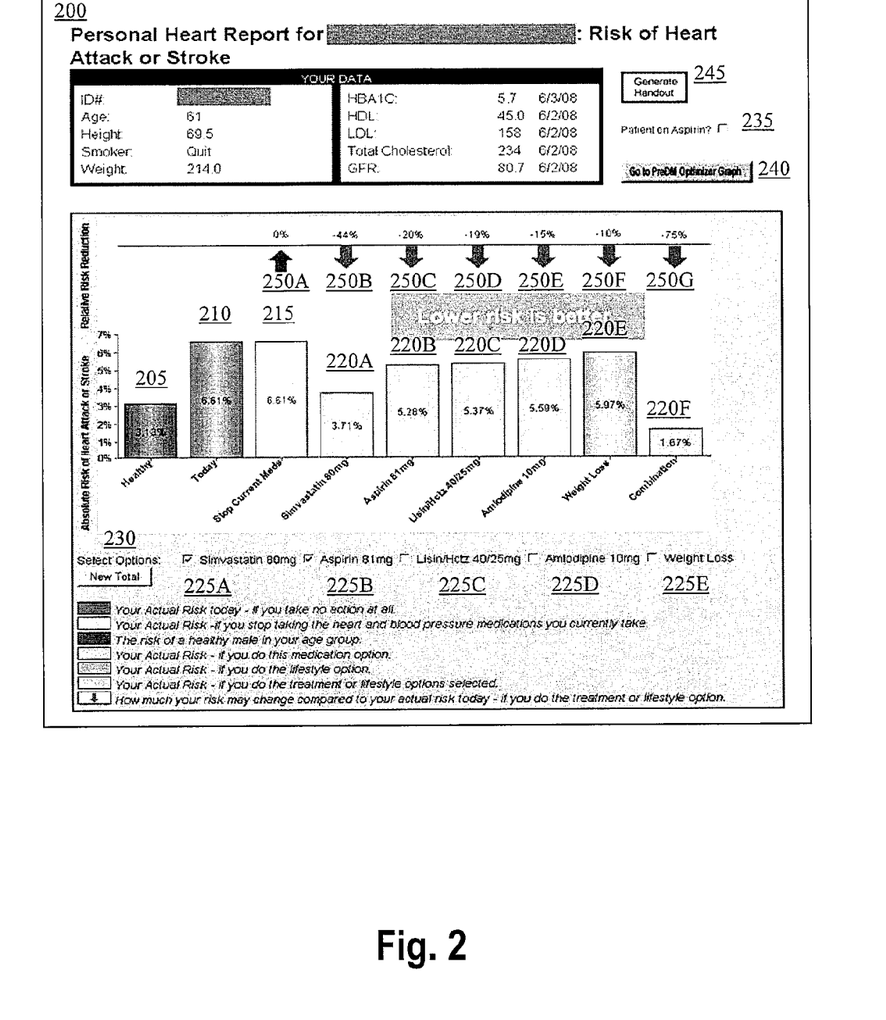
FIG. 2 illustrates an embodiment of a user interface.
Figure 3:
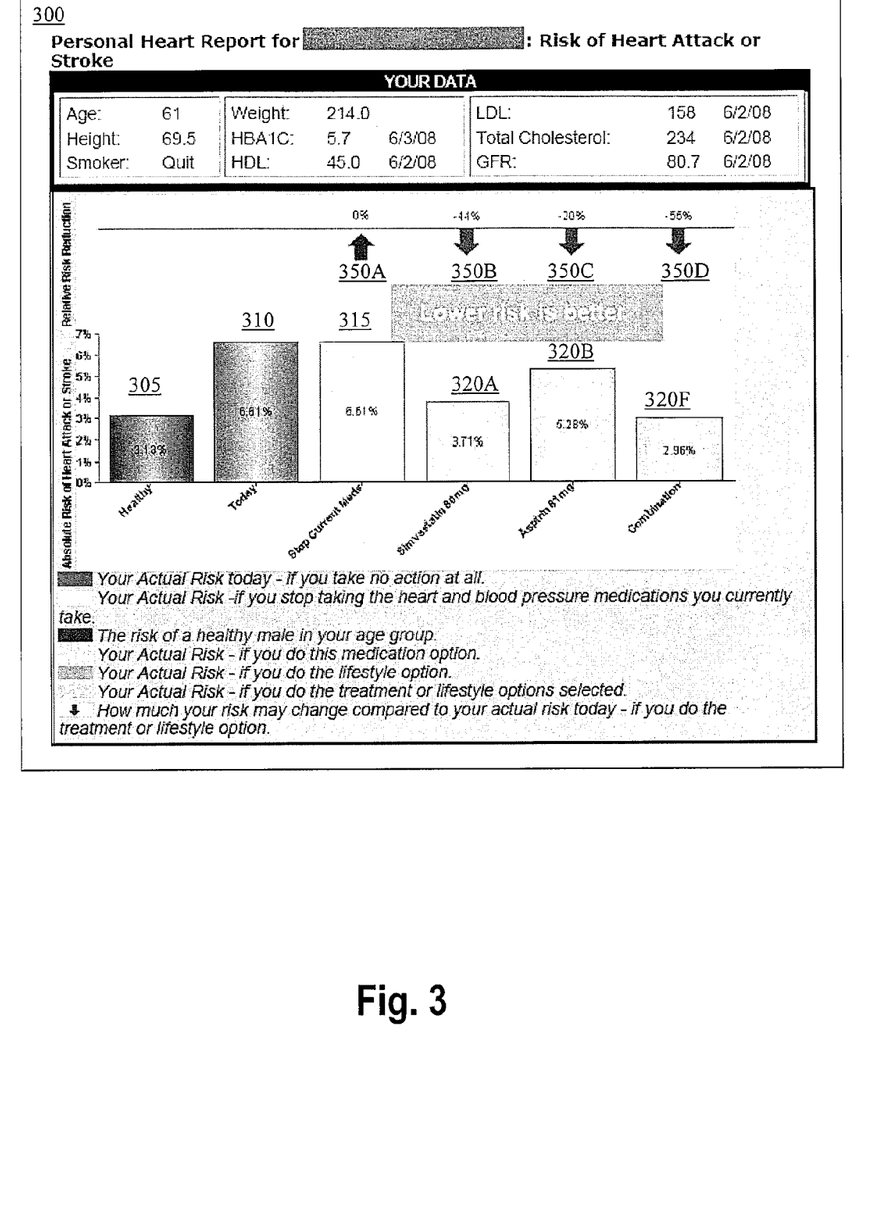
FIG. 3 illustrates an embodiment of a user interface.

FIG. 2 illustrates an example user interface. FIG. 2 represents an embodiment of the graphical representation 200 that may be created by an embodiment. In this embodiment, graphical representation 200 displays the relative magnitude of benefit score values for a plurality of interventions 220A-220F. The graphical representation 200 of FIG. 2 is typically generated for use by a healthcare provider or representative such as a physician or care manager whereas a more simplified graphical representation 300, shown in FIG. 3 and described further herein, is typically generated for direct presentation to a patient or member of a healthcare plan. To generate the graphical representations of FIG. 2 and FIG. 3, a query is issued by requesting entity 190, received by query component logic 140 and executed by query execution logic 150. The examples of FIG. 2 and FIG. 3 are generated from response 120 received from query response logic 160. Graphical representation 200 may be embodied in a graphical display or video display of a computer display unit, in printed output on a computer print device, or in other tangible forms.

Each bar is a graphical representation of a metric determined by query execution logic 150 based on patient information 170 and intervention information 180 and represents an absolute risk of a condition occurring for the patient. In the example of FIG. 2, the condition is heart attack or stroke. In an embodiment, "Today" bar 210 indicates a benefit score value for the current patient at present.

In an embodiment, "Healthy" bar 205 shows the expected risk for a person of preferred health having characteristics matching the patient, such as age and gender. Preferred health may be defined by the provider. For example, preferred health may represent the average healthy person, or may represent a more obtainable goal. The Healthy bar 205 can provide a meaningful reference point to the patient who may not know whether a particular percentage risk is low or high. For example, younger patients might have a high risk for their age but a seemingly low risk of having an event in the next few years. The reference point can be represented as a bar on a graph, or a line across the graph cutting across the other bars, or as a number on the display.

Graphical representation 200 further includes a "Stop Current Meds" bar 215, which indicates what the patient's risk would be by discontinuing taking all the preventive medications that he or she is currently taking and that are capable of analysis by Archimedes Optimizer. The risk associated with stopping current medications may be equal to or greater than a patient's current risk. In an embodiment, all medications that the patient is currently on may be represented with the Stop Current Meds bar 215, so that the discontinued use of a particular medication may result in a lower risk. In such a case, the "Stop Current Meds" bar 215 may represent a lower risk than the risk represented by the "Today" bar 210.

Graphical representation 200 shows several possible interventions 220A-220E. Each intervention 220A-220F has a bar that represents the risk of, in this case, heart attack or stroke, over a predefined period of time. In the graphical representation 200 shown in FIG. 2, intervention 220A provides the greatest benefit to the particular patient associated with FIG. 2, although for other patients another intervention may provide the best benefit. Different benefits are best for different patients because the benefit scores forming a basis for the risk bars in graphical representation 200 are based upon individualized information. For example, a different patient may benefit more from weight loss than taking a prescription drug. Another patient may benefit more by cessation of smoking.

Graphical representation 200 further shows a combination intervention bar 220F that represents multiple interventions 220A and 220B. In some cases, a patient may benefit from more than one intervention. FIG. 2 shows an example of this. The combination intervention bar 220F represents the combined benefit of intervention 220A representing the patient taking Simvastatin 80 mg and intervention 220B representing the patient taking Aspirin 81 mg.

Combination intervention bar 220F is not necessarily the result of adding the benefits of the included interventions, but rather takes into account overlapping effects. For example, intervention X and intervention Y may each result in a 50% decrease in risk of having heart disease. However, the combination of interventions X and Y may result in only a 51% decrease in risk if the benefits of the interventions are derived from treating the same underlying cause of the disease. Combination intervention bar 220F takes this overlap into consideration.

Although FIG. 2 represents a risk of heart attack or stroke, embodiments representing any disease or condition and associated interventions may be used. For example, the interface may represent a personal diabetes report, HIV report, or lung cancer report. Further, multiple diseases or conditions may be represented in the same embodiment.

In other embodiments, other graphical approaches to compare risk values may be used. For example, a line graph may represent today's risk and a predicted risk associated with an intervention. A physician may compare the two scenarios and generate a report using a line graph for the patient to enable the patient to make an educated decision about a health issue.

Further, in other embodiments, the orientation and size of graphical representation 200 may be different than the vertical bars shown in FIG. 2. If a large number of interventions is available, then horizontal bars may be used, and may allow for downward scrolling of a viewing interface rather than side-to-side scrolling. In an embodiment, each bar may be numbered. In an embodiment, a key may be presented in order to fit more bars on a screen. In an embodiment, the scale may be different than shown in FIG. 2.

In an embodiment, there are three categories of users that interact with the system. "Provider users" represent users of the system that are associated with a healthcare provider, including doctors, nurse practitioners, nurses, case managers, and other healthcare professionals. "Member users" represent patients and those acting on behalf of patients. "Administrator users" represent users of the system that determine which features are available to other users, and have the ability to set and change global preferences. In an embodiment, the types of users may be expanded beyond those described, and the users described may be broken down into sub-categories of users. For example, users acting on behalf of patients may have a different level of access than the patient.

In an embodiment, preferences such as the type of visual representation as well as the orientation may be saved by users of the system. In an embodiment, preferences may be associated with user login information and may be saved on a computer-readable storage medium that is coupled to the data processing apparatus 100 or on a client computer using a browser in the form of a "cookie". A provider user may have a preference for a particular type of graph, while a member user sending a request for the graphical representation from a personal computer 190 may have prefer a different presentation. In an embodiment, colors of bars, available interventions, and other preferences may also be saved.

In an embodiment, other preferences may be saved by an administrator user on behalf of the health care provider. An administrator user may choose to show all interventions available, or only those interventions that have been deemed to meet a threshold of acceptability. For example, a particular intervention may have high cost but low effectiveness. In such a case, the intervention may be omitted from graphical representation 200. Further, drugs to which a patient is allergic may be omitted from the graphical representation, or shown as a typically effective, but unavailable intervention. Showing an intervention as ordinarily effective but unavailable may be useful when a patient merely would have an undesirable and mild but non-threatening reaction to a particular medication. The member user may decide with the provider user whether the reaction is worth the side effects of the intervention.

Side effect information may also be shown and even incorporated into graphical representation 200. For example, in an embodiment, a bar representing a "side effect score" may be shown alongside an associated intervention bar. Side effect information may also be shown to the side of the bar, or as a pop-up in response to selecting an intervention bar, or by selecting checkboxes created for the purpose of displaying side effect information. In one embodiment, side effects can be weighted manually and displayed accordingly alongside the intervention information to allow the member user and the provider user to compare interventions while taking into consideration the member user's side effect preferences.

This graphical representation 200 further provides the provider user and member user with sufficient common information about alternative treatments to make informed collaborative decisions about care. Each non-combination intervention 220A-220E has an associated check box 225A-225E. Interventions are selected using the check-boxes. Typically a provider user reviews the graphical representation 200 and selects one or more of the check-boxes for the purpose of generating a customized report for the member user in the form of FIG. 3. When an intervention 225A and 225B is checked and a "New Total" button 230 is pressed, the combination intervention bar 220F is recalculated and presented in an updated version of the graphical representation 200, or in the form of FIG. 3. Alternatively, a checkbox, when checked, may cause the total to be recalculated without requiring the user to press button 230.

In other embodiments, other selection methods may be used. For example, a user of the system may, instead of checking checkboxes 225A and 225B, select bar 220A and bar 220B, and in response the query response logic 160 and processor 130 of FIG. 1 perform the immediate recalculation of bar 220F without the need to press button 230. Indicators may be used to show that a bar is selected or unselected. Example indicators include highlighting the bar or changing the color of the bar.

Arrows 250A-250G represent a relative risk reduction for the condition associated with the intervention. For example, when intervention boxes 225A, 225B are checked and the new total button 230 is pressed, combination bar 220F is calculated and shows a 1.67% chance of having a heart attack or stroke in the next five years. The 1.67% risk is a −75% reduction over today's risk, as shown by arrow 250G which corresponds to combination bar 220F.

Button 240 may be used to generate a different report for the same patient. For example, pressing button 240 may generate a pre-diabetic report that shows interventions that may be beneficial for patients that are pre-diabetic. In other embodiments, buttons are not required. For example, a drop-down list may be used to select reports, and a single option may be selected to generate more than one report or one report representing more than one condition.

Checkbox 235 may be used to instantly alter the results of the intervention graph, based on patient information at the time of the office visit. For example, a patient who has been advised to take aspirin regularly may not be doing so. Since aspirin is an over-the-counter medication for which consumption may not be monitored like a prescription drug, the provider user may not be able to depend on the data in the system, and should therefore ask the patient if he is taking aspirin regularly. Depending on the patient's response, checkbox 235 may be checked. Checking box 235 causes a re-calculation of affected interventions.

Missing patient data is filled in with values that follow the same distribution as closely matching individuals from a sample population. To account for normal variation, fifty clones of the patient with this distribution of values are created. For each intervention, a confidence threshold comprising a mean benefit calculated from the clones is reported if it is more than two standard deviations above the benefit threshold. A confidence score may also be displayed adjacent to one or more risk presentation bars.

As an additional check, in an embodiment, a benefit score is not reported for blood pressure medications, statin, or insulin if blood pressure, LDL cholesterol, or HbA1c values respectively are missing. Logic or rules that define how to process a graphical representation in the presence of missing data or relating to confidence thresholds are ignored if a care gap already exists for an intervention. In such cases, benefit for that information is reported.

In an embodiment, the bars in FIG. 2 may represent chances of not having the condition within the next five years instead of chances of having the condition within the next five years. In such a case, a full bar is desirable, and represents greater health.

In another embodiment, the measurement of the bars may be presented as odds instead of as a percentage. In such an embodiment, query response logic 160 will form a response indicating presentation preferences. Depending on local culture or norms associated with a population or a location of deployment of the system 100, other methods of conveying the metrics associated with the bars may be used, such as showing a group of icons shaped like humans, each representing an individual, with a subset of these icons identified by color or other indicator as having the condition. For example, the affected icons could be colored red while the rest are colored green.

In another embodiment, a bar may show a medication that a patient is taking for which the dose is sub-optimal. In such a case, the bar may show only increased benefit, show full benefit, or show both the increased benefit and an overlay of the full benefit.

More than one condition may be represented on a single report. For example, if risks for heart attack and diabetes are shown on the same report, then a particular intervention, such as weight loss, may result in benefiting the patient for both conditions. However, one condition may provide more benefit than the other condition from the weight loss intervention; in an embodiment, the weight loss bar 220E may comprise two (2) bars with an indicator such as color, number, or text label on each bar for distinguishing which condition each bar represents. Conveying that one intervention may benefit two conditions may have a profound impact on the patient, compelling the patient to action.

FIG. 3 represents another embodiment of a graphical representation. A personal heart attack or stroke report is displayed in the example graphical representation 300. In contrast to graphical representation 200, in one embodiment, graphical representation 300 is a personalized view, containing only selected information for a particular patient or member that the provider user was considering at the time of viewing graphical representation 200. In an embodiment, the graphical representation of FIG. 3 is generated in response to a query 110 issued by the medical practitioner to data processing apparatus 100 by selecting the generate handout button 245. Query 110, which is received by query component logic, includes information indicating the interventions that query execution logic 150 is to consider. Query response logic 160 returns a response 120 with reduced presentation information. The receiving entity will generate a graphical representation 300. The resulting graphical representation 300 is a reduced presentation of graphical representation 200.

For example, the healthy bar 305, today bar 310, and stop current meds bar 315 have the same general appearance, meaning and function as the healthy bar 205, today bar 210, and stop current meds bar 215 in graphical representation 200. However, fewer intervention bars are shown in graphical representation 300. Specifically, only the interventions for which checkboxes were chosen in graphical representation 200 are shown, and interventions that were not selected are not shown. Thus, interventions 320A and 320B are shown in graphical representation 300 because corresponding checkboxes are checked in graphical representation 200.

In one embodiment, the combination bar 320F is always shown in the personalized view. The personalized view may be used to generate a printed handout for patients to take home, and also includes arrows 350A-350D to remind the patient of the relative risk reduction for each intervention or the combination of interventions.

In an embodiment, graphical representation 300 of FIG. 3 can help the patient see and feel good about the impact of what they are already doing. For example, a physician may review the displayed information with a patient in a medical office setting, communicating, "The good news Mr. Jones is that the aspirin you are taking has reduced your risk to 60% of what it was when you first came to my office". Another possible display representing what the patient's risk would be if she had never taken any preventive interventions, which is a slightly different value compared to what the risk would be if she stopped today. Finally there is the historical risk display which would shows the patients risk as computed on a previous date or dates. These risks can be shown as bars on a graph, lines across the graph or other methods for displaying information can be used such as overlaying the current risk onto the historical risk, each represented by a bar.

The graphical representations shown in FIG. 2 and FIG. 3 may be displayed on a computer screen, printed from a printing device, or stored as a data file. The graphical representations also may be sent via email or internal messaging system. The graphical representations need not be displayed on a computer screen in order to be stored or printed. For example, Button 245 in FIG. 2 may be pressed to print graphical representation 300 to a printing device, without viewing graphical representation 300 on a computer monitor. A single action such as pressing a button may also be used to store or view the graphical representation 300. Likewise, graphical representation 200 may be viewed, saved, or printed by a one-touch operation from a query results screen, such as the one featured in FIG. 4.

Figure 4:
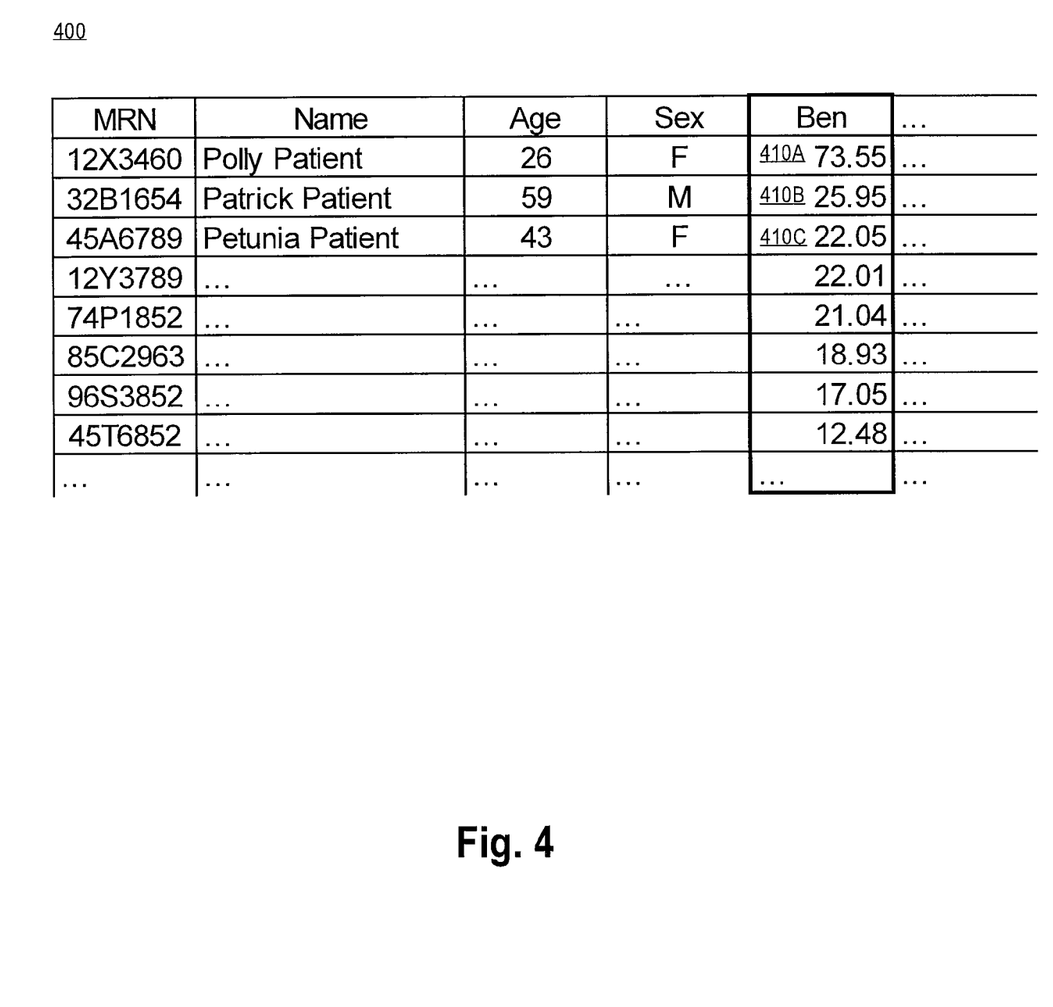
FIG. 4 illustrates an embodiment of a user interface.

FIG. 4 illustrates an example graphical user interface. FIG. 4 represents an example query result view called a panel view. In an embodiment, user may request information based on any attribute of real patients that is stored in patient information 170, typically for the purpose of identifying one or more real patients who may benefit from preventive medical advice or intervention. For example, a user may search for females, for people under the age of 50, for the person with a particular medical record number, or for people who meet a health related metric threshold. In addition, any number of attributes may be combined to focus the query results.

In an embodiment, records of patients may be retrieved based on benefit score, risk, or quality of life score threshold alone. FIG. 4 shows the results of a search for patients meeting a particular benefit score threshold, sorted by highest benefit score. Benefit scores 410A, 410B, and 410C reflect the available beneficial interventions for their respective patients, who are further identified by a medical record number and any other information configured to display in response to the query. The benefit score, alongside patient information, allows medical practitioners to identify patients that would benefit significantly from one or more interventions, based on the information about patients currently in the system.

In the panel view of FIG. 4, all available benefits may be shown, or only a combination of the benefits may be shown. The threshold may be configured as a preference, may be hard-coded into the system, or may be chosen at the time of search.

In some cases, a patient may have very little benefit from an intervention. In such cases, a healthcare provider may omit showing the intervention. An example would be giving antihypertensive medications if the patient has normal blood pressure. In order to avoid showing trivial benefits, a lower threshold of benefit is established for each intervention below which benefit is not reported.

Although graphical representation 300 is shown as providing a subset of information contained in graphical representation 200, this need not be the case. The provider user may be presented with more or less options and more or less information than a member user. Further, the way the information is presented, combined, or determined may be different, depending on the user.

For example, FIG. 4 shows an overall benefit score 410A for a user. A provider may find this information useful in determining that a member has interventions available that will provide a positive impact on the member's health. A single metric such as an overall benefit score that represents all risks with unequal weights assigned to those risks helps the provider proactively contact members which will benefit the most from intervention.

On the other hand, a single number may have little impact on a member. Further, a member may have different goals than the provider, and prefer a different weighting system, rendering the unequally weighted benefit score inappropriate for such a member. For example, a member patient may be motivated by vanity more than health, and opt to take an oral medication that is known to cause liver complications in order to eradicate a toenail fungus. The provider, on the other hand, may be more concerned about the liver complications, and therefore assign a very low weight to the condition. Therefore, a member may be presented with a graphical representation 300 that represents the goals of the patient. One or more conditions, or a category of conditions may be presented, with each condition receiving equal weight.

In an embodiment, the timeline presented to provider users and member users may differ. For example, a member may be short sighted, and concerned only about health over the next 2 years. However, a provider, expecting to insure the member for the remainder of the member's life, may instead be more concerned about the long term health of the member, making a 30 year timeline more appropriate.

In an alternative embodiment, a member user may directly access an interface that generates reports containing the data shown in FIG. 2 and FIG. 3. In such a case, the administrator user may choose to allow only a subset of interventions to be shown. Showing a subset of interventions may encourage one behavior over another, and also avoid causing the patient to self-medicate without discussing treatment with a medical practitioner. Alternatively, a member user may have access to the same information as a provider user.

In one embodiment, a member user can connect to the apparatus from a personal computer or other device such as a handheld device or smart phone using a network such as the Internet. The member user may be provided the graphical representation 300. Alternatively, the member user may be provided a separate interface that allows the member user to compare his current risk using a today bar 210 with the reduced risk associated with one intervention. As another option, the member user may be shown only the today bar 210 and the combination bar 220F. Any other combination or subset of bars 205-220F may be shown in various embodiments, each showing a today bar 210 and at least one other bar.

Architecture

In one embodiment, the apparatus 100 is implemented entirely on the same computer. In an embodiment, a client/server architecture may be used, but is not required. For example, software instructions for implementing the logical elements of FIG. 1, patient information and intervention information may be distributed using computer readable storage media such as a CD-ROM. A computer containing query component logic 140, query execution logic 150, and query response logic 160, with intervention information 180, may use patient information 170 from a CD-ROM to generate the graphical representation 200, 300, or 400. In some embodiments, patient information 180 may be accessed over a network.

Alternatively, client/server architecture may be used. For example, one or more of the query component logic 140, query execution logic 150, query response logic 160, intervention information 180, and patient information 170 may exist on separate computers, connected via any communication medium. For example, the separate computers may be connected via the Internet, a dedicated network connection, or a proprietary network connection.

In one embodiment, the apparatus comprises a client computer that is coupled to and retrieves data from a central data source. Alternatively, the apparatus comprises a server, sending the response 120 to a separate computer.

In another embodiment, patient information 170 and intervention information 180 used in creating the graphical representation 200 is compiled at regular intervals and stored on a separate computer than the computer which compiled the information, providing a system that has semi-dynamic information. In such a case, multiple scenarios may be compiled to create the feel of completely dynamic information. For example, the today bar 210, stop current meds bar 215, and intervention bars 220A-220F may yield different results if the "patient on aspirin" box 235 is checked. If two scenarios are compiled, one assuming the patient is taking aspirin and the other assuming the patient is not taking aspirin, then the user of the system may select the box and see results as if the information was completely dynamic. The same method may be used to determine other scenarios, resulting in near-dynamic information.

In another embodiment, a request may be sent from one computer and received by another computer which generates and returns the graphical representation 200 using real-time information. In this case, the information contained in the graphical representation is truly dynamic, representing real-time information as the information becomes available. For example, a provider user may revise or update patient information during an office visit with the patient. The updated information is then available via graphical representation 200. In one such embodiment, the updated information is reflected immediately after new information is available, requiring no request to update graphical representation 200.

Example Technical Assumptions

Patient Data Quality

In an embodiment, the quality of patient information 170 is maintained by the processor 130 performing one or more patient data quality checks. In an embodiment, patient information 170 is received from a healthcare provider, modified and stored before system 100 begins operation. In an embodiment, following range checks is performed on patient health data that is provided by a healthcare provider; the resulting checked data is stored as patient information 170 for use in system 100.

| Field | Low | High |
| --- | --- | --- |
| Height | 44 inches | 87 inches |
| Weight | 80 lbs | 600 lbs |
| Diastolic blood pressure | 40 mm Hg | 130 mm Hg |
| Systolic blood pressure | 80 mm Hg | 220 mm Hg |
| Fasting plasma glucose | 50 mg/dL | 300 mg/dL |
| HDL cholesterol | 20 mg/dL | 130 mg/dL |
| LDL cholesterol | 50 mg/dL | 400 mg/dL |
| Total cholesterol | 70 mg/dL | 500 mg/dL |
| Creatinine | 0 mg/dL | 8 mg/dL |

In data received from a healthcare provider, fields that are blank or that fail the range check are replaced with values that follow the same distribution as closely matching individuals from a sample population.

Medication Usage History

In an embodiment, Archimedes Optimizer factors in a patient's medication usage when determining risk of health outcomes. Medication usage history is established by considering within a 10-year period the first date used and the total days supplied. History is considered for insulin, metformin, sulfonylureas, ACE inhibitors, beta blockers, calcium channel blockers, diuretics (thiazide and thiazide-like, loop, potassium-sparing, and combination), ARBs, glitizones, fibrates, niacin, and statins.

Benefit Score

Benefit Score is reported per intervention recommended by the Archimedes Optimizer. The Intervention Benefit Score attempts to predict how much better the patient's health will be in 5 years if he/she receives the intervention compared to the patient's health in 5 years if he/she did not receive the intervention. The calculation is a weighted combination of the expected decrease in risk of the various outcomes from receiving the intervention. Weights are selected to approximate the expected difference in the quality of life. Quality of life scores ordinarily range between zero and one. A healthy person has a quality of life score of one, and a quality of life score of zero represents death. The Archimedes Optimizer multiplies these scores by one thousand to put them on a larger scale (0 to 1000). In other embodiments, quality of life scores may have a range other than the range between zero and one. Furthermore, the Archimedes Optimizer is not limited to a scale of 0 to 1000, and may even be configured to scale or convert quality of life scores using non-linear functions.

The benefit should be interpreted assuming the patient receives the intervention with 100% compliance starting today as compared to never starting the intervention. The context of this comparison is an assumption that the patient continues taking medications they are currently taking indefinitely but does not start any other intervention except the one in question. For example the evaluation of simvastatin in a patient currently taking only lisinopril is really a comparison of (take lisinopril and simvastatin for the next five years) vs. (take lisinopril only for the next five years).

Total Benefit Score

The Total Benefit Score attempts to predict how much better the patient's health will be in 5 years if he/she receives all the interventions recommended by the Archimedes Optimizer (also shown on the Patient Detail View), compared to the patient's health in 5 years if he/she received none of those interventions.

Thresholds

Two types of thresholds are applied in the model. If the thresholds are not met, intervention benefits are not reported, unless a PST care gap is already active for the recommendation.

The benefit threshold is determined using cost-benefit analysis. Using cost data, a relationship between the benefit threshold for each intervention and its cost effectiveness may be established. In an embodiment, the threshold for weight loss is BMI>=25. In an embodiment, under the operation of a second threshold, smoking cessation is listed for anyone who smokes. These thresholds can be subsequently modified based on feedback from a healthcare provider.

The following are some of the assumptions used to perform the cost-benefit analysis of Archimedes Optimizer interventions.

|  | Compliance | Visits and Tests |
| --- | --- | --- |
| ACE inhibitor | 100% | For all BP meds: Initiation: 3 visits, chemistry panel (chem 7), Change to/addition of: 2 visits |
| Beta blocker | 100% | |
| Calcium channel blocker | 100% | |
| Diuretic | 100% | |
| ACE inhibitor/diuretic | 100% | |
| Aspirin | 100% | |
| Statin | 100% | Initiation or change to: 1 visit, 1 chemistry panel, 1 liver panel |
| Insulin | 100% | Initiation: 3 visits, 4 chemistry panels |
| Oral diabetes medication | 100% | Initiation: 2 visits, 2 chemistry panels |

Risk in a Normal Healthy Person

In an embodiment, in graphical representation 200 and graphical representation 300 the risk of the health outcome in a normal healthy individual of the same age and gender as the patient is provided for comparison. In an embodiment, the risk is calculated as the nth percentile (for example, n=10) of the risk distribution in the patient sub-population of that age and gender.

Interventions and Outcomes

The following matrix summarizes the interventions and the outcomes that each intervention affects. Risk of an outcome with an intervention is reported only for those interventions that have a check mark in the outcome column. When computing the benefit of an intervention, only those outcomes that have a check mark in the intervention row are considered. Included are: Cardiovascular Disease: includes myocardial infarctions and strokes (fatal and non-fatal); Development of Diabetes Mellitus (actual, not diagnosed); Diabetes Mellitus Complications: includes foot ulcers, blindness, and end-stage renal disease.

|  | CVD | Development of DM | DM Complications |
| --- | --- | --- | --- |
| ACE inhibitor | ✓ |  | ✓ |
| Aspirin | ✓ |  |  |
| Beta blocker | ✓ |  |  |
| Calcium channel blocker | ✓ |  |  |
| Diuretic | ✓ |  |  |
| ACE inhibitor/diuretic | ✓ |  | ✓ |
| Statin | ✓ |  |  |
| Insulin | ✓ |  | ✓ |
| Oral diabetes medication | ✓ |  | ✓ |
| Weight loss | ✓ | ✓ | ✓ |
| Smoking cessation | ✓ |  |  |

Hardware Overview

Figure 5:
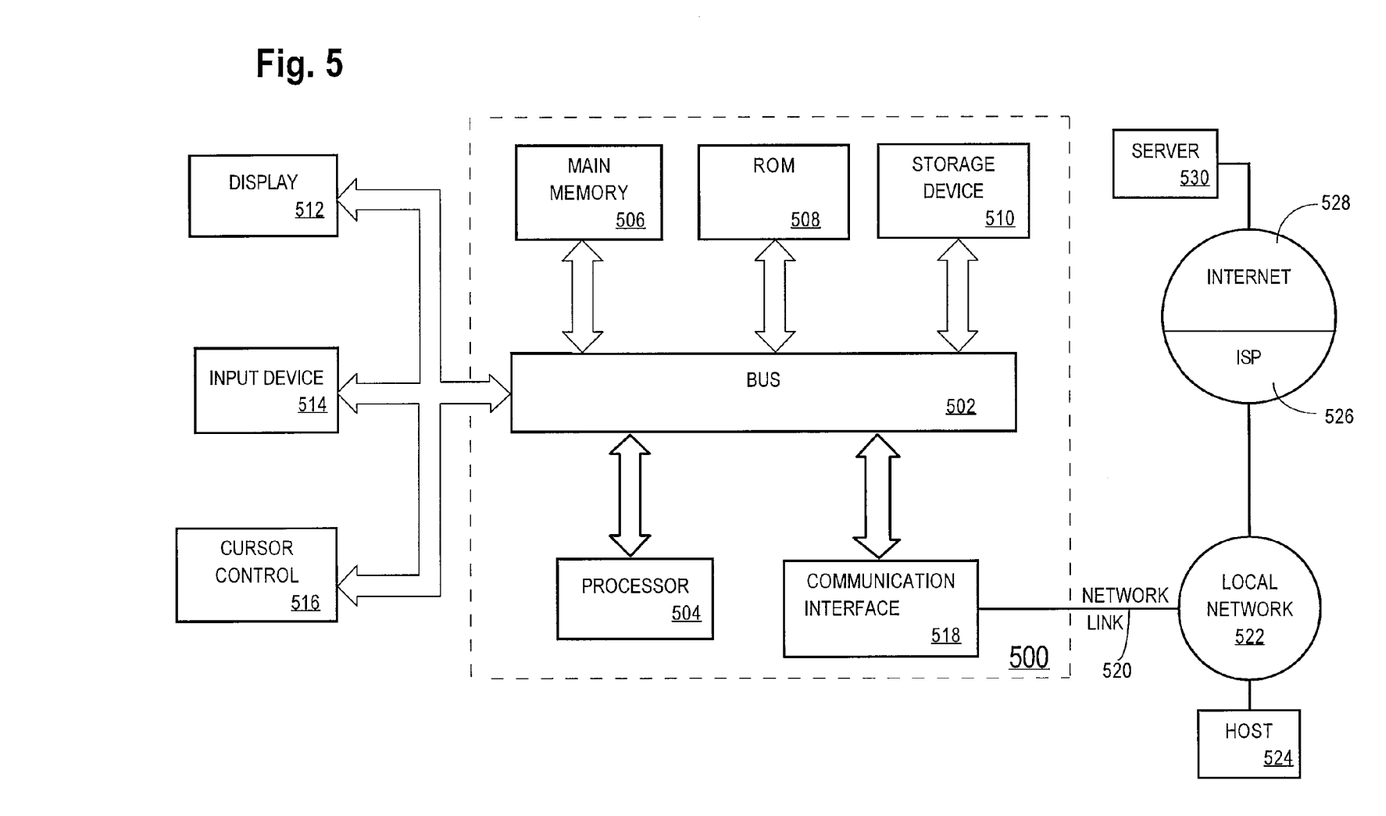
FIG. 5 illustrates a computer system upon which an embodiment may be implemented.

FIG. 5 is a block diagram that illustrates a computer system 500 upon which an embodiment of the invention may be implemented. Computer system 500 includes a bus 502 or other communication mechanism for communicating information, and a processor 504 coupled with bus 502 for processing information. Computer system 500 also includes a main memory 506, such as a random access memory (RAM) or other dynamic storage device, coupled to bus 502 for storing information and instructions to be executed by processor 504. Main memory 506 also may be used for storing temporary variables or other intermediate information during execution of instructions to be executed by processor 504. Computer system 500 further includes a read only memory (ROM) 508 or other static storage device coupled to bus 502 for storing static information and instructions for processor 504. A storage device 510, such as a magnetic disk or optical disk, is provided and coupled to bus 502 for storing information and instructions.

Computer system 500 may be coupled via bus 502 to a display 512, such as a cathode ray tube (CRT), for displaying information to a computer user. An input device 514, including alphanumeric and other keys, is coupled to bus 502 for communicating information and command selections to processor 504. Another type of user input device is cursor control 516, such as a mouse, a trackball, or cursor direction keys for communicating direction information and command selections to processor 504 and for controlling cursor movement on display 512. This input device typically has two degrees of freedom in two axes, a first axis (e.g., x) and a second axis (e.g., y), that allows the device to specify positions in a plane.

The invention is related to the use of computer system 500 for implementing the techniques described herein. According to one embodiment of the invention, those techniques are performed by computer system 500 in response to processor 504 executing one or more sequences of one or more instructions contained in main memory 506. Such instructions may be read into main memory 506 from another machine-readable medium, such as storage device 510. Execution of the sequences of instructions contained in main memory 506 causes processor 504 to perform the process steps described herein. In alternative embodiments, hard-wired circuitry may be used in place of or in combination with software instructions to implement the invention. Thus, embodiments of the invention are not limited to any specific combination of hardware circuitry and software.

The term "machine-readable medium" as used herein refers to any medium that participates in providing data that causes a machine to operation in a specific fashion. In an embodiment implemented using computer system 500, various machine-readable media are involved, for example, in providing instructions to processor 504 for execution. Such a medium may take many forms, including but not limited to storage media. Storage media includes both non-volatile media and volatile media. Non-volatile media includes, for example, optical or magnetic disks, such as storage device 510. Volatile media includes dynamic memory, such as main memory 506. All such media must be tangible to enable the instructions carried by the media to be detected by a physical mechanism that reads the instructions into a machine.

Common forms of machine-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, and EPROM, a FLASH-EPROM, any other memory chip or cartridge, or any other medium from which a computer can read.

Various forms of machine-readable media may be involved in carrying one or more sequences of one or more instructions to processor 504 for execution. For example, the instructions may initially be carried on a magnetic disk of a remote computer. The remote computer can load the instructions into its dynamic memory and send the instructions over a telephone line using a modem. A modem local to computer system 500 can receive the data on the telephone line and use an infra-red transmitter to convert the data to an infra-red signal. An infra-red detector can receive the data carried in the infra-red signal and appropriate circuitry can place the data on bus 502. Bus 502 carries the data to main memory 506, from which processor 504 retrieves and executes the instructions. The instructions received by main memory 506 may optionally be stored on storage device 510 either before or after execution by processor 504.

Computer system 500 also includes a communication interface 518 coupled to bus 502. Communication interface 518 provides a two-way data communication coupling to a network link 520 that is connected to a local network 522. For example, communication interface 518 may be an integrated services digital network (ISDN) card or a modem to provide a data communication connection to a corresponding type of telephone line. As another example, communication interface 518 may be a local area network (LAN) card to provide a data communication connection to a compatible LAN. Wireless links may also be implemented. In any such implementation, communication interface 518 sends and receives electrical, electromagnetic or optical signals that carry digital data streams representing various types of information.

Network link 520 typically provides data communication through one or more networks to other data devices. For example, network link 520 may provide a connection through local network 522 to a host computer 524 or to data equipment operated by an Internet Service Provider (ISP) 526. ISP 526 in turn provides data communication services through the world wide packet data communication network now commonly referred to as the "Internet" 528. Local network 522 and Internet 528 both use electrical, electromagnetic or optical signals that carry digital data streams. The signals through the various networks and the signals on network link 520 and through communication interface 518, which carry the digital data to and from computer system 500, are exemplary forms of carrier waves transporting the information.

Computer system 500 can send messages and receive data, including program code, through the network(s), network link 520 and communication interface 518. In the Internet example, a server 530 might transmit a requested code for an application program through Internet 528, ISP 526, local network 522 and communication interface 518.

The received code may be executed by processor 504 as it is received, and/or stored in storage device 510, or other non-volatile storage for later execution. In this manner, computer system 500 may obtain application code in the form of a carrier wave.

In the foregoing specification, embodiments of the invention have been described with reference to numerous specific details that may vary from implementation to implementation. Thus, the sole and exclusive indicator of what is the invention, and is intended by the applicants to be the invention, is the set of claims that issue from this application, in the specific form in which such claims issue, including any subsequent correction. Any definitions expressly set forth herein for terms contained in such claims shall govern the meaning of such terms as used in the claims. Hence, no limitation, element, property, feature, advantage or attribute that is not expressly recited in a claim should limit the scope of such claim in any way. The specification and drawings are, accordingly, to be regarded in an illustrative rather than a restrictive sense.

What is claimed is:

1. A data processing apparatus, comprising:
   one or more processors;
   query component logic coupled to the one or more processors and configured to receive a request comprising patient identification information associated with a patient;
   query execution logic coupled to the one or more processors and the query component logic, and configured to determine a first metric, based at least in part on the patient identification information, wherein the first metric comprises a current health related metric for the patient; determine two or more different medical intervention metrics, each based at least in part on a different associated medical intervention, the patient identification information and simulated data obtained by simulating effects that may be caused by applying the different associated medical intervention to a representative virtual population of patients, representing a predicted health related metric for the patient as if the different associated medical intervention was performed in the future;
   wherein the representative virtual population of patients is a projected, computer-generated population of patients;
   query response logic coupled to the one or more processors and the query execution logic, configured to electronically send a response that causes a computer to create a graphical representation based on the first metric and the medical intervention metrics, wherein the graphical representation concurrently presents the first metric and the medical intervention metrics.

2. The apparatus of claim 1, wherein the query response logic is further configured to cause the computer to display the graphical representation.

3. The apparatus of claim 1, wherein the query response logic is further configured to cause the computer to send the graphical representation to a printing device.

4. The apparatus of claim 1, wherein the display is a bar chart comprising a bar depicting the first metric; and for each of the medical intervention metrics, two or more second bars respectively depicting one of the associated medical intervention metrics.

5. The apparatus of claim 4, wherein the request is received from the patient.

6. The apparatus of claim 4, wherein the request is received from a healthcare provider.

7. The apparatus of claim 1, wherein the query execution logic is further configured to determine a historical metric, based at least in part on the patient identification information, wherein the historical metric comprises a historical value associated with one of: the first metric; or an intervention metric, and the graphical representation concurrently presents the first metric, the medical intervention metrics, and the historical metric.

8. The apparatus of claim 7, wherein the display is a bar chart comprising a first bar depicting the first metric; for each of the medical intervention metrics, an intervention bar depicting the associated medical intervention metric; and a historical bar depicting the historical metric; wherein the first bar is visually overlaid on top of the historical bar.

9. The apparatus of claim 1, wherein one of the intervention metrics is a combination metric based on a combination of two or more of the intervention metrics other than the combination metric.

10. The apparatus of claim 9, wherein the combination metric is represented by a value other than a sum of the two or more intervention metrics on which the combination metric is based.

11. The apparatus of claim 1, wherein the query component logic is further configured to receive a second request comprising intervention identification information, wherein the intervention identification identifies two or more selected interventions associated with the medical intervention metrics;
wherein the query response logic is further configured to cause the computer to create a graphical representation based on the first metric and the intervention information, wherein the graphical representation concurrently presents the first metric and only intervention metrics for the selected interventions.

12. The apparatus of claim 1, wherein one of the medical intervention metrics is a stop current medication metric, representing a predicted health related metric for the patient when the patient stops taking one or more particular medications.

13. The apparatus of claim 1, wherein the query execution logic is further configured to determine a health metric, representing a simulated health related metric for a person of preferred health having one or more predetermined characteristics that match characteristics of the patient.

14. The apparatus of claim 1, wherein the health related metric represents a risk of occurence of at least one of:
 (a) death;
 (b) myocardial infarction;
 (c) stroke;
 (e) renal failure; or
 (f) amputation.

15. The apparatus of claim 1, wherein the health related metric represents a change in health-related quality of life.

16. The apparatus of claim 1, wherein the health related metric represents a change in life expectancy.

17. A non-transitory computer-readable medium carrying one or more sequences of instructions for processing health related data, which instructions, when executed by one or more processors, cause the one or more processors to carry out the steps of:
 receiving a request comprising patient identification information associated with a patient;
 determining a first metric, based at least in part on the patient identification information, wherein the first metric comprises a current health related metric for the patient;
 determining two or more medical intervention metrics, each based at least in part on a different associated medical intervention, the patient identification information and simulated data obtained by simulating effects that may be caused by applying the different associated medical intervention to a representative virtual population of patients, representing a predicted health related metric for the patient as if the different associated medical intervention was performed in the future;
 wherein the representative virtual population of patients is a projected, computer-generated population of patients;
 electronically sending a response that causes a computer to create a graphical representation based on the first metric and the medical intervention metrics, wherein the graphical representation concurrently presents the first metric and the medical intervention metrics.

18. The non-transitory computer readable medium of claim 17 further comprising instructions which, when executed by the one or more processors, cause the one or more processors to cause the computer to display the graphical representation.

19. The non-transitory computer readable medium of claim 17 further comprising instructions which, when executed by the one or more processors, cause the one or more processors to cause the computer to send the graphical representation to a printing device.

20. The non-transitory computer readable medium of claim 17, wherein the display is a bar chart comprising a bar depicting the first metric; and for each of the medical intervention metrics, two or more second bars respectively depicting one of the associated medical intervention metrics.

21. The non-transitory computer readable medium of claim 20, wherein the request is received from the patient.

22. The non-transitory computer readable medium of claim 20, wherein the request is received from a healthcare provider.

23. The non-transitory computer readable medium of claim 17 further comprising instructions which, when executed by the one or more processors, cause the one or more processors to determine a historical metric, based at least in part on the patient identification information, wherein the historical metric comprises a historical value associated with one of: the first metric; or an intervention metric, and the graphical representation concurrently presents the first metric, the medical intervention metrics, and the historical metric.

24. The non-transitory computer readable medium of claim 23, wherein the display is a bar chart comprising a first bar depicting the first metric; for each of the medical intervention metrics, an intervention bar depicting the associated medical intervention metric; and a historical bar depicting the historical metric; wherein the first bar is visually overlaid on top of the historical bar.

25. The non-transitory computer readable medium of claim 17, wherein one of the medical intervention metrics is a combination metric based on a combination of two or more of the medical intervention metrics other than the combination metric.

26. The non-transitory computer readable medium of claim 25, wherein the combination metric is represented by a value other than a sum of the two or more medical intervention metrics on which the combination metric is based.

27. The non-transitory computer readable medium of claim 17 further comprising instructions which, when executed by the one or more processors, cause the one or more processors to:
 receive a second request comprising intervention identification information, wherein the intervention identification identifies one or more selected interventions associated with the medical intervention metrics; and
 cause the computer to create a graphical representation based on the first metric and the intervention information, wherein the graphical representation concurrently presents the first metric and only intervention metrics for the selected interventions.

28. The non-transitory computer readable medium of claim 17, wherein one of the medical intervention metrics is a stop current medication metric, representing a predicted health related metric for the patient when the patient stops taking one or more particular medications.

29. The non-transitory computer readable medium of claim 17 further comprising instructions which, when executed by the one or more processors, cause the one or more processors to determine a health metric, representing a simulated health related metric for a person of preferred health having one or more predetermined characteristics that match characteristics of the patient.

30. The non-transitory computer readable medium of claim 17, wherein the health related metric represents a risk of occurence of at least one of:
   (a) death;
   (b) myocardial infarction;
   (c) stroke;
   (e) renal failure; or
   (f) amputation.

31. The non-transitory computer readable medium of claim 17, wherein the health related metric represents a change in health-related quality of life.

32. The non-transitory computer readable medium of claim 17, wherein the health related metric represents a change in life expectancy.

* * * * *